(12) United States Patent
Ateya et al.

(10) Patent No.: US 9,110,010 B2
(45) Date of Patent: Aug. 18, 2015

(54) ELECTRICAL DETECTION USING CONFINED FLUIDS

(75) Inventors: Daniel A. Ateya, Alexandria, VA (US); Peter B Howell, Jr., Gaithersburg, MD (US); Frances S. Ligler, Potomac, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1768 days.

(21) Appl. No.: 12/118,028

(22) Filed: May 9, 2008

(65) Prior Publication Data

US 2009/0011430 A1 Jan. 8, 2009

Related U.S. Application Data

(60) Provisional application No. 60/917,341, filed on May 11, 2007.

(51) Int. Cl.
*G01N 27/327* (2006.01)

(52) U.S. Cl.
CPC ................... *G01N 27/3276* (2013.01)

(58) Field of Classification Search
None
See application file for complete search history.

(56) References Cited

U.S. PATENT DOCUMENTS

| | | | |
|---|---|---|---|
| 2002/0127144 A1* | 9/2002 | Mehta | 422/81 |
| 2003/0044832 A1* | 3/2003 | Blankenstein | 435/6 |
| 2004/0106189 A1 | 6/2004 | Dodgson et al. | |
| 2004/0132220 A1* | 7/2004 | Fish | 436/525 |
| 2005/0239046 A1 | 10/2005 | Sachs et al. | |
| 2006/0102519 A1* | 5/2006 | Tonkovich et al. | 208/107 |
| 2006/0175601 A1 | 8/2006 | Lieber et al. | |
| 2007/0017633 A1 | 1/2007 | Tonkovich et al. | |

FOREIGN PATENT DOCUMENTS

WO   WO 00/56444   *   9/2000   ............... B01J 19/00

OTHER PUBLICATIONS

The definition of "meter" provided by the online dictionary at dictionary.cambridge.org [retrieved on Jun. 2, 2010]. Retrieved from the Internet: <URL: dictionary.cambridge.org/dictionary/british/mete_1>.*
Berdat et al., "Label-free detection of DNA with interdigitated microelectrodes in a fluidic cell" Lab Chip, 8, 302-308 (2008).
Boehm et al., "On-chip microfluidic biosensor for bacterial detection and identification" Sensors and Actuators B, 126, 508-514 (2007).
Koch et al., "Design and fabrication of a micromachined Coulter counter," Journal of Micromechanics and Microengineering, 9, 159-161 (1999).
Mott et al., U.S. Appl. No. 11/423,225 (filed Jun. 9, 2006).

(Continued)

*Primary Examiner* — Robert T Crow
(74) *Attorney, Agent, or Firm* — US Naval Research Laboratory; Joseph T. Grunkemeyer (57) ABSTRACT

A device having: a laminar flow channel for liquids; two or more electrodes; a confining fluid inlet; a sample inlet; and a meter for measuring the impedance of any fluid between the electrodes. The device may have one or more specific binding sites, or it may have sheathing and unsheathing fluid transporting structures. A method of: providing the device; flowing a confining fluid and a conductive liquid that may contain cells or particles through the channel as described herein; and measuring the impedance between the electrodes.

29 Claims, 10 Drawing Sheets

(56) References Cited

OTHER PUBLICATIONS

Nieuwenhuis et al., "Integrated Coulter counter based on 2-dimensional liquid aperture control," Sensors and Actuators B, 102, 44-50 (2004).
Radke et al., "A high density microelectrode array biosensor for detection of *E. coli* O157:H7," Biosensors & Bioelectronics, 20, 1662-1667 (2005).
Saleh et al., "Quantitative sensing of nanoscale colloids using a microchip Coulter counter," Review of Scientific Instruments, 72, 4449-4451 (2001).
Yang et al., "Electrical/electrochemical impedance for rapid detection of foodborne pathogenic bacteria," Biotechnology Advances, 26, 135-150 (2008).
PCT Search Report and Written Opinion, 2009.

* cited by examiner

ELECTRICAL DETECTION USING CONFINED FLUIDS

This application claims the benefit of U.S. Provisional Application No. 60/917,341, filed on May 11, 2007. This provisional application and all other publications and patent documents referenced throughout this application are incorporated herein by reference.

FIELD OF THE INVENTION

The devices and methods disclosed herein generally related to electrical detection of particles by the use of confining fluids.

DESCRIPTION OF RELATED ART

Electrical detection techniques have been used for the transduction of biological information. Some common historical uses include: monitoring the metabolic activity of bacteria in solution; examination of the electrical properties of cells; counting, sizing and sorting suspended cells; and monitoring cell proliferation and morphology in culture. The ability to precisely fabricate electrode geometries embedded in surfaces and in micron-scale chambers has enabled the enhancement of sensitivity and resolution compared with that of similar macro-scale techniques.

A microfluidic biochip that utilized impedance spectroscopy for the detection of the *Listeria innocua* in a microfluidic chamber has been demonstrated (Gomez et al., "Microfluidic biochip for impedance spectroscopy of biological species," *Biomedical Microdevices*, 3 (2001): 201-209; Gomez et al., "Microscale electronic detection of bacterial metabolism," *Sensors and Actuators B*, 86 (2002): 198-208). In this work, different concentrations of bacteria were cultured to promote bacterial growth and metabolism. The samples were then flowed into a microfluidic chamber and impedance measurements confirmed that suspensions with higher concentrations of bacteria gave rise to higher conductivity as compared to the low conductivity control buffer.

Several groups have used electrical techniques in hybrid sensors that contain cells cultured directly on arrays of microfabricated electrodes. These cell-based sensors utilize two levels of signal transduction; the first is the transduction of a signal or biological response by the cells themselves and the second is electrochemical transduction at the electrode interface, whereby electrical measurements can be monitored to detect information regarding the cellular response. These techniques rely on the fact that cells bound to a substrate impart an electrical impedance that can be measured depending on the number, spatial orientation and morphology of the cells. Electric cell-substrate impedance sensing (ECIS) has been used to monitor the morphology and density of cells cultured directly on gold electrodes that were deposited in modified culture dishes (Giaever et al., "Monitoring fibroblast behavior in tissue culture with an applied electric field," *Proceedings of the National Academy of Sciences*, 81 (1984): 3761-3764). The system monitored the electrical impedance between two electrodes and showed that as cells attach and spread on the electrode surface, they alter the effective area available for current flow and correspondingly alter the impedance.

A method and apparatus for measuring changes in cell volume in a microchamber using electrical impedance was used to monitor cell volume regulation mechanisms, to screen potential drug candidates for their effect on ion channel activity, as well as the growth of suspended bacteria and inhibition of growth in the presence of antibiotics (Sachs et al, U.S. Patent Pub. No. 2005/0239046). The sensitivity of the method is governed by the chamber height relative to size of the cells or particles to be detected. Since the sensitivity of the measurement was governed by the well-confined dimensions of the microfluidic chamber, such microfluidic sensors are limited in their use for screening unprocessed biological samples, as clogging is increasingly problematic when a complex sample is flowed through very small channels (Mukhopadhyay, "When microfluidic devices go bad," *Analytical Chemistry-A Pages*, (2005): 429A-432A).

There are other reports of impedance-based methods for detection of bacteria (Yang et al., "Electrical/electrochemical impedance for rapid detection of foodborne pathogenic bacteria," *Biotechnology Advances*, 26 (2008): 135-150). Detection of *E. coli* BL21(DE3) down to concentrations of $10^4$-$10^5$ CFU/mL with impedance measurements in a microchamber containing electrodes and an antibody functionalized surface was reported (Boehm et al., "On-chip microfluidic biosensor for bacterial detection and identification," *Sensors and Actuators B: Chemical*, 126 (2007): 508-514). The surface of planar electrodes has been functionalized with analyte specific antibodies, demonstrating the specific detection of pathogenic, *E. coli* O157:H57 with simple impedance measurements (Radke et al., "A high density microelectrode array biosensor for detection of *E. coli* O157:H7," *Biosensors & Bioelectronics*, 20 (2005): 1662-1667). The biosensor was able to discriminate between cellular concentrations of $10^4$-$10^7$ CFU/mL. This sensitivity is insufficient for bacterial detection in practical applications.

The Coulter technique has also been adapted to microfluidic systems in a variety of studies, providing a means for counting, sizing, separation and sorting of cells and even nanoscale particles, including viruses on microchips (Koch et al., "Design and fabrication of a micromachined Coulter counter," *Journal of Micromechanics and Microengineering*, 9 (1999): 159-161; Saleh et al., "Quantitative sensing of nanoscale colloids using a microchip Coulter counter," *Review of Scientific Instruments*, 72 (2001): 4449-4451). A practical limitation of the Coulter techniques lies in the fact that the sensitivity is governed by the ratio of particle size to that of the aperture through which the particles must flow. As the aperture size approaches the dimensions of the particle to be analyzed, the sensitivity increases. A tradeoff is therefore presented, as there is an increased tendency for clogging as aperture size decreases.

In a similar configuration to a Coulter setup, the integration of electrodes on opposite sides of a microfluidic channel for electric impedance spectroscopy has been demonstrated to determine suspended particle and single-cell electrical properties with a higher spatial resolution and increased frequency range possible than previous techniques (Ayliffe, "Microelectric impedance spectroscopy: Biological materials and cells," Ph.D. Thesis, University of Utah, (1999)). The device demonstrated the ability to distinguish between different cell types, detect cell viability (live or dead), and estimate both membrane capacitance and cytoplasmic resistance. The work demonstrated the spatial resolution provided by electrical detection techniques in microfluidic systems, and the ability to isolate and study single cells.

A Coulter counter with a dynamically controlled, two-dimensional liquid aperture for impedance-based detection of cells and particles has been reported (Nieuwenhuis et al., "Integrated Coulter counter based on 2-dimensional liquid aperture control," *Sensors and Actuators B*, 102 (2004): 44-50). The work reports finite element modeling and an experimental ability to control the liquid aperture. However, the experimentally obtained electrical measurements were not sensitive, citing parasitic substrate capacitances due to the device design and fabrication.

A significant body of research has focused on the control of fluidic interfaces in micron-scale geometries. In particular, it has been demonstrated that due to the laminar nature of flow, mixing between parallel flow streams in microfluidic devices is generally limited to that of diffusion (Brody et al., "Diffusion-based extraction in a microfluidic device," *Sensors and Actuators A*, 58 (1997): 13-18). The flow regime at this scale can generally be characterized by low Reynolds numbers (Re) and high Peclet numbers (Pe). In other words, inertial forces are negligible compared to viscous forces, and convective, bulk transport of liquid dominates mass transfer, as compared to mass transfer by diffusion (Atencia et al., "Controlled Microfluidic Interfaces," *Nature*, 437 (2005): 648-655). This combination of effects allows exquisite control over fluid interfaces in microfluidic systems.

SUMMARY OF THE INVENTION

Disclosed herein is a device comprising: a laminar flow channel for liquids having an interior surface; one or more specific binding sites on the interior surface that can bind to a cell or particle of interest; two or more electrodes on the interior surface; a confining fluid inlet positioned to flow a confining fluid through the channel; a sample inlet positioned to flow a conductive liquid between the confining fluid and the interior surface; and a meter for measuring the impedance of any fluid between the electrodes.

A device comprising: a laminar flow channel for liquids having an interior surface; one or more specific binding sites on the interior surface that can bind to a cell or particle of interest, wherein the specific binding sites are arranged in regions of the interior surface containing different types of specific binding sites; two or more electrodes on the interior surface; a sample inlet positioned to flow a conductive liquid in contact with the interior surface; two lateral confining fluid inlets positioned to flow a confining fluid in contact with the interior surface and the conductive liquid such that the conductive liquid contacts only one region at a time; and a meter for measuring the impedance of any fluid between the electrodes.

Also disclosed herein is a device comprising: a laminar flow channel for liquids; a confining fluid inlet positioned to flow a confining fluid through the channel; a sample inlet positioned to flow a liquid sample through the channel; two or more electrodes in the channel; at least one sheathing fluid transporting structure positioned so that the confining fluid forms a sheath around the liquid sample within a liquid-sheathed portion of the channel between the electrodes in which the liquid sample does not contact the channel; at least one unsheathing fluid transporting structure positioned so that the sheath is removed from around the liquid sample; and a meter for measuring the impedance of any fluid between the electrical electrodes. The electrodes are positioned to be in contact with the liquid sample in non-liquid-sheathed portions of the channel.

Also disclosed herein is a method comprising: providing a flow channel comprising an interior surface having two or more electrodes and one or more specific binding sites; flowing a conductive fluid through the channel and in contact with the electrodes and the binding sites; flowing a confining fluid through the channel at a rate that confines the conductive fluid to a confined portion of the channel that is adjacent to the electrodes and the binding sites; and measuring the impedance between the electrodes.

Also disclosed herein is a method comprising: providing a flow channel comprising an interior surface having two or more electrodes; flowing a liquid sample through the channel and in contact with the electrodes; flowing the confining fluid through the channel at a rate that confines the liquid sample to a confined portion of the channel that is adjacent to the electrodes; and measuring the impedance between the electrodes. The channel comprises: at least one sheathing fluid transporting structure positioned so that the confining fluid forms a sheath around the liquid sample within a liquid-sheathed portion of the channel between the electrodes in which the liquid sample does not contact the channel; and at least one unsheathing fluid transporting structure positioned so that the sheath is removed from around the liquid sample; and wherein the electrodes are positioned to be in contact with the liquid sample in non-liquid-sheathed portions of the channel on either side of the sheathed portion.

BRIEF DESCRIPTION OF THE DRAWINGS

A more complete appreciation of the invention will be readily obtained by reference to the following Description of the Example Embodiments and the accompanying drawings.

FIG. 2 shows finite element analysis of the flow configuration shown in FIG. 1. A) Mesh generated with a four-electrode impedance measurement configuration. B) Resulting solution of electric potential distribution for the model shown in FIG. 2A); demonstrating confinement of electric field lines in the thin conductive fluid layer

FIG. 7 shows (A) Isometric schematic of the stripe-based sheath flow design. (B) Computational model of the sample solution being sheathed in the sheath solution using Tiny-3D.

FIG. 8 shows (A) Isometric schematic of the chevron-based sheath flow design. The arrows indicate introduction of the respective sheath and sample solutions. (B) Shape of the sample stream modeled as a function of the number of chevron pairs. The outlines depict the shape of the sample stream resulting from flow ratios of 4.5:1:4.5 (top) and 9.5:1:9.5 (bottom) with 1-6 chevron pairs.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail. The terms "liquid" and "fluid" are used interchangeably.

The disclosed methods and devices may enable label-free electrical detection of cells or particles in sensors whose sensitivity is no longer governed by the dimensions of a microfabricated channel itself, but rather the well-defined flow profile of a conductive fluid stream in the channel. The methods may be broadly applicable for point-of-care diagnostic devices and continuous, reagent free monitors for biowarfare detection. The techniques can rely on simple electronics and thus eliminate the use of bulky optical components (such as lasers, lenses, filters, cameras, etc.) which are common to many current biosensor systems. The ability for electronic control and measurement may be well suited to portable systems, unattended monitoring, UAV mounted sensors, continuous water monitoring and for environmental detection of biothreat agents, in general. There may be applications to techniques for cell-based screening and high-throughput assays for drug discovery, as well as fundamental studies of cell physiology.

Figure 1:
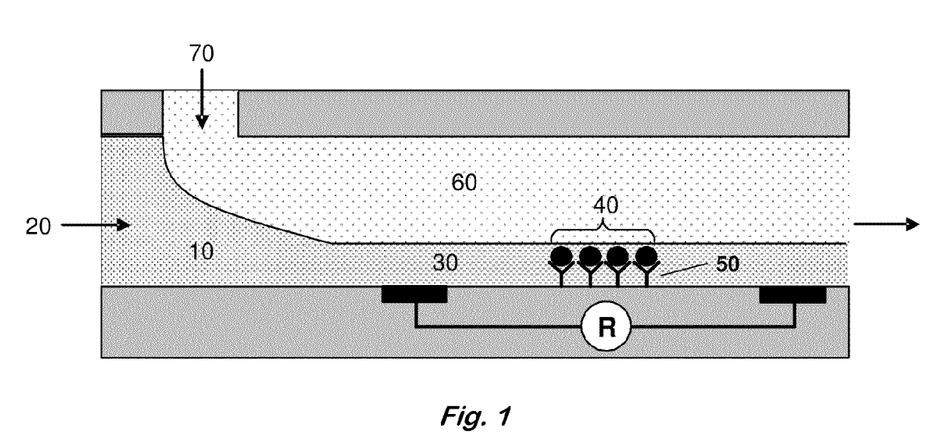
FIG. 1 shows a flow configuration whereby adjusting the ratio of flow rates between inlet 2 and inlet 1 focuses a conductive fluid to a thin layer, comparable in height to cells specifically bound in a sensing region between two electrodes.

Channels may be fabricated in, for example, plastics, glass, silicon, or other materials with dimensions that are large enough to avoid clogging issues when manipulating unprocessed samples. In one embodiment, a sample containing target particles or cells may be flowed through the channel over specific binding sites patterned in the channel. After binding of the target to the binding sites, conductive and non-conductive fluids can be introduced into the channel from two or multiple inlets that produce flow configurations conducive to high sensitivity electrical detection of bound species. An example of this embodiment of the invention can be seen in an affinity assay configuration, for instance, where specific binding of target cells in the sample may be defined in the sensing region between two electrodes embedded in a channel as depicted in FIG. 1.

The higher conductivity ionic buffer 10 is introduced from inlet 1 20 and is confined to a thin layer 30 containing the cells or particles 40 bound to the specific binding sites 50 by a low-conductivity liquid flow 60 introduced from inlet 2 70. By adjusting the relative flow rates of the two fluids, flow confinement can be used to decrease the height or cross-section of the conductive liquid in the region containing the binding sites through which the electrical current will be focused. By using a low-conductivity liquid to confine a higher conductivity ionic buffer in the channel, the conductive path can be tailored for electrical measurements to a thin laminar fluid layer comparable in height to that of cells or particles present in the sensing region of the channel. Since the sensitivity of such particle detection methods is governed by the size of the particle relative to the conductive path, the invention enables new label-free microfluidic sensors with tunable sensitivities by simply adjusting the flow rates and configuration of the input fluids.

A variety of binding sites and liquids may be used with the device. Any binding site that will specifically bind to a cell or particle of interest and that can be immobilized to the interior surface may be used. Suitable binding sites include, but are not limited to, antibodies, DNA molecules, sugars, antimicrobial peptides, aptamers, cell receptors, molecularly imprinted polymers (such as those disclosed in U.S. Pat. Nos. 6,310,110; 6,583,191; and 6,660,780), antigens, biochemical ligands, avidin, and lectin. Antigens may be used, for example, to bind to cells that already have a corresponding antibody on their surface. Avidin may be used to bind to cells or particles having biotin bound to the surface. The particles may also be glass beads, latex particles, or magnetic particles. Such particles may be, but are not limited to, about 1 nm to 100 μm in diameter.

The flow channel utilizes laminar flow as opposed to turbulent flow to avoid mixing of the two liquids that are flowing through the channel. The device may be used in several embodiments of the method. In one embodiment, a liquid sample is flowed through the channel with no other liquids. After allowing any of the cells or particles in the sample to bind to the binding sites, the conductive and confining fluids are flowed as in FIG. 1 and the impedance measured. In another embodiment, the liquid sample and the confining fluid are flowed at the same time to allow for binding, followed by flowing the conductive and confining fluids for measuring impedance. Either of these two-step methods may be used when it is desired to measure the impedance in the conductive liquid instead of in the medium of the liquid sample. For example, the liquid sample may not have a high enough conductivity. In another embodiment, the liquid sample and confining liquid are flowed together in one step for both cell binding and impedance measurement. In this embodiment, the liquid sample is the conductive fluid. This method can allow for real-time monitoring of the presence of the cell or particle.

The binding sites may be placed on the interior surface either between the electrodes or between the sample inlet and the electrodes. The change in impedance in the presence of the bound cell may be partially due to a perturbation of the flow downstream from a bound cell. The conductive liquid layer may be thinner behind the particle leading to an increase in impedance. By placing the binding sites in advance of the electrodes, the impedance increase may be primarily or mostly due to this perturbation.

Any conductive fluid or liquid sample may be used that does not cause denaturization of the binding sites. A liquid sample may contain a cell or particle that specifically binds to the binding sites. Suitable liquid samples may be aqueous or organic, and may comprise materials including, but not limited to, culture media, clinical samples, food extracts, beverages, environmental samples, fuel such as diesel fuel, an industrial process stream, and seawater. Suitable conductive liquids include, but are not limited to, aqueous salt solutions, ionic buffers, physiological saline, and ionic liquids.

The confining fluid may have a lower conductivity than the conductive fluid and/or liquid sample, and may have a viscosity that does not create turbulence when flowing adjacent to the conductive fluid and/or liquid sample. Suitable confining fluids include, but are not limited to, deionized water, glycerol, aqueous solutions of sugars such as fructose, alcohols, and aqueous poly(vinyl alcohol) solutions.

The electric field and resulting electrode potentials were simulated using finite element analysis of the confined flow in a model system similar to that shown in FIG. 1. The relation between the electric potential distribution, $\sigma(x,y,z)$ resulting from a low frequency electric field, and the conductivity distribution, $\sigma(x,y,z)$ of a purely resistive, source-free region can be modeled using Laplace's equation:

$$\sigma\nabla^2\phi+\nabla\sigma\nabla\phi=0 \quad \text{(Equation 1)}$$

If the conductivity distribution, $\sigma(x,y,z)$ of the fluid profile in a channel, and the boundary conditions on the surfaces of the channel are known, the electric potential distribution within the channel can be determined uniquely. This is known as the "forward problem" in volume conductor theory (Kauppinen et al., "Sensitivity distributions of impedance cardiography using band and spot electrodes analyzed by a three-dimensional computer model," *Annals of Biomedical Engineering*, 26 (1998): 694-702), which was used for demonstration of one embodiment. With predetermined flow ratios, an iterative sequence of simulations was used to monitor the channel conductance as the confinement flow of distilled water focused the conductive ionic buffer to different layer heights that approached the dimensions of bound cells or particles. In this manner, the progressively increasing resistance profile obtained during the scan can be monitored for characteristic variations from that of a surface with no bound particles. The simulated results from this model demonstrate the main principle of this invention.

Figure 2:
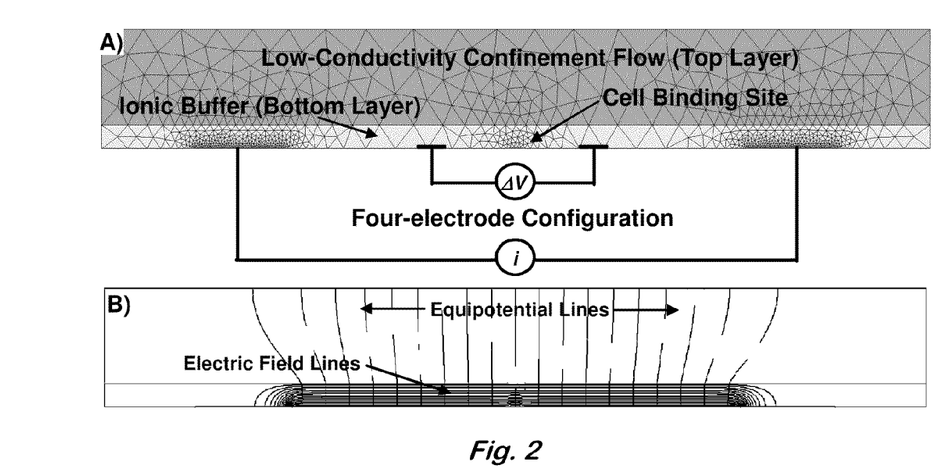
Figure 3:
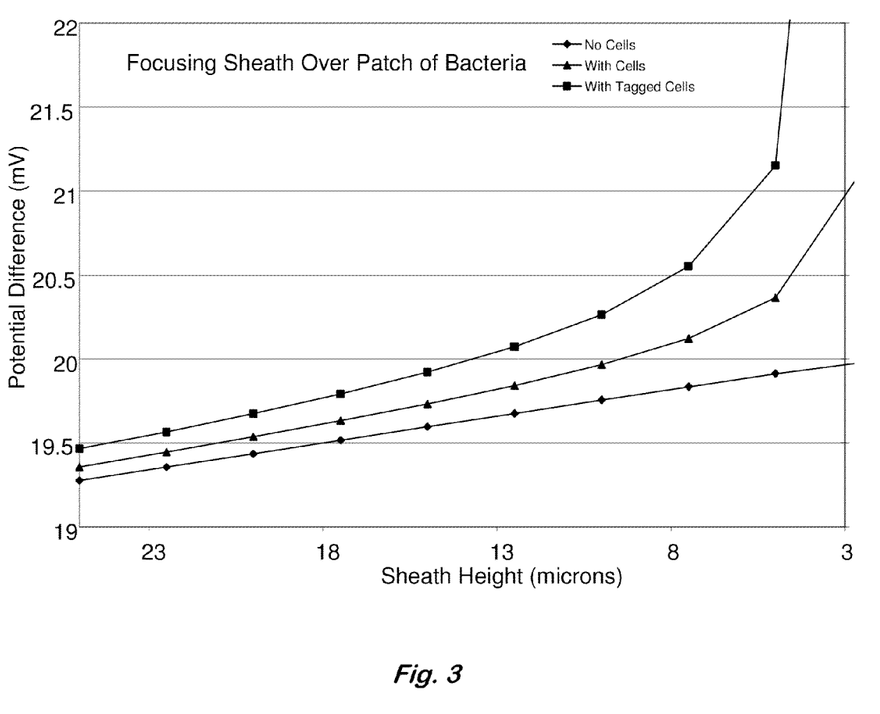
FIG. 3 shows finite element simulation of the potential difference, $\Delta V$ from FIG. 2A that would be measured while progressively decreasing the height of the conductive sheath flow in three situations: (1) with no cells bound in the sensing region (2) with 10 µm long by 1 µm high patch of bacteria bound in the sensing region (3) with 10 µm long by 2 µm high patch of bacteria bound in the sensing region

FIG. 2 shows an initial model based on the sensing configuration presented in FIG. 1. FIG. 2A shows the mesh generated in the microchannel with a height of 125 μm and length of 1 mm. A four-electrode configuration is utilized in which the outer current electrodes (embedded in the bottom of the channel) pass an electric current and are arbitrarily separated by a distance of 600 μm. A cell-binding site is located between two voltage-sensing electrodes that noninvasively monitor the electric potential difference in the region of the channel in which the binding site is located. In this model the voltage-sensing electrodes are separated by a distance of 100 μm, and the cell binding site is 10 μm long. The analysis swept through a series of conductive liquid sheath layer heights for three binding situations: 1) With no cells bound in the sensing region; 2) with a close-packed layer of particles 1 μm in thickness and filling the length of the 10 μm binding region; and 3) with a close-packed layer of particles 2 μm in thickness and filling the length of the 10 μm binding region. FIG. 2B shows resulting electric potential distribution, where the vertical lines represent lines of equal potential and the dense, horizontal lines represent the electric field lines which are well contained within the thin conductive liquid sheath over the surface containing the electrodes as opposed to the non-conductive deionized water used to focus the conductive layer. Results shown in FIG. 3 demonstrate a linear change in the potential drop measured between the two voltage-sensing electrodes, as the sheath height decreases with no cells in the sensing region. The presence of cells gives rise to a nonlinear deviation from the linear control curve, indicating their presence in the sensing region.

In a two-electrode system, impedance measurements are accomplished by passing an electric current through the same electrode-solution interfaces with which simultaneous voltage measurements are made. This electric current produces a polarization of the electrode-solution interface that is unpredictably combined with the desired voltage measurement. Similarly, in a two-electrode system, nonspecific binding on the surface of the electrode cannot be discerned from polarization effects at the electrochemical interface. Complex current paths are also set up around cells, and measurements may vary dramatically based on factors such as cell adhesion, orientation, morphology, etc. In this manner, the sensitivity and resolution of this type of two-electrode measurement may be compromised and difficult to quantify with a great deal of certainty.

It may be desirable to isolate specific binding events in a well-defined region isolated from, but located within, a standard four-electrode configuration for impedance measurements. The standard four-electrode configuration passes a steady-state current through two outer current electrodes while measuring the potential difference between the two inner electrodes in the configuration. The current is driven and maintained by an active current source and the voltage can be measured with high input impedance electronics; thus eliminating any undesirable polarization effects on the measurement of interest. In fact, the four-electrode configuration may have an additional benefit. It can minimize the effect of non-specific binding/fouling on electrodes. The active current source maintains the current injected into the channel, regardless of any bound species at the interface, and the voltage-sensing electrodes utilize such small bias currents for measurements (<1 pA), that they noninvasively measure the potential in the channel that has been generated by the current injection electrodes.

The methods may be employed in parallel configurations for continuous monitoring of larger sample volumes and for multiple target analytes simultaneously. The same one-step and two-step methods described above are applicable to parallel configurations. A variety of device configurations are possible, including but not limited to the following.

Figure 4:
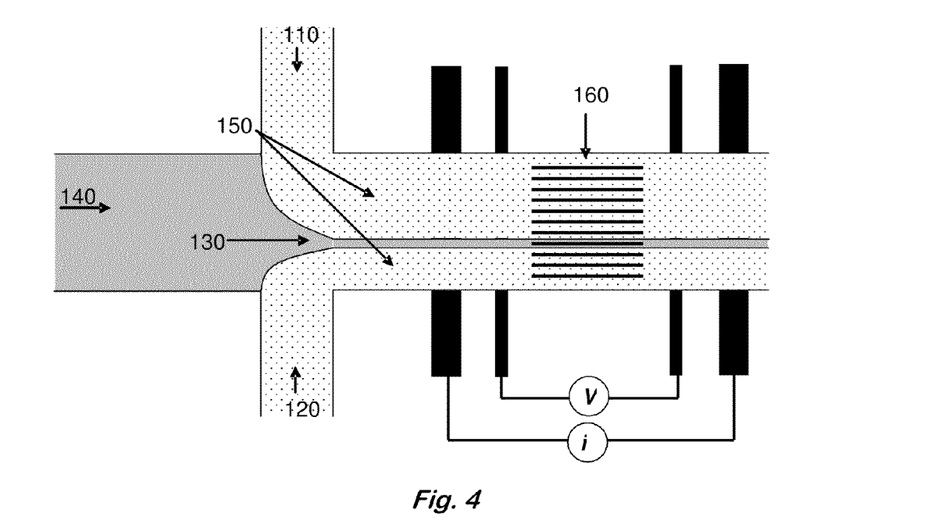
FIG. 4 shows a schematic diagram of an embodiment that focuses the conductive fluid with multiple fluid inlets to create a stream that may be directed to desired regions on the surface of the channel. The flow of a conductive ionic buffer can be confined and scanned laterally across the surface of a channel, for focused electrical interrogation of specific regions in a capture antibody array.

The ability to both focus a conductive flow path in both height (FIG. 1) and lateral dimensions could enable the following device configuration. FIG. 4 is a schematic showing the top view of focusing the conductive fluid flow both vertically and laterally. With the addition of two inlets 110, 120 for laterally focusing the conductive fluid 130, the conductive path laterally may be confined laterally and still sheath the height of the conductive path from above (as depicted in FIG. 1). The resulting well-defined stream may then be scanned laterally across the width of the channel. The configuration is shown in FIG. 4, where the conductive ionic buffer is introduced in inlet 1 140, and the low-conductivity confinement liquid 150 is introduced in inlets 2 and 3. By simply adjusting the relative flow rates of inlets 2 and 3, the path can be scanned laterally over the channel surface (in the y-direction of the channel), following very specific paths in the sensing region of the channel. Either the entire array may be scanned, or any subset of the regions may be scanned during either binding or impedance measurement. By creating a well-defined array of capture molecules 160 in the sensing region, this configuration may be used for high-throughput, impedance-based detection of a variety of targets in a single, biological sample. This embodiment also presents a paradigm for impedance-based detection, whereby the same measurement electrodes can be used to interrogate various isolated regions in a channel, as desired. This format will be particularly useful for looking at the positive and negative controls simultaneously while screening samples for multiple targets. This configuration may also be used with only lateral confinement and no vertical confinement.

Figure 5:
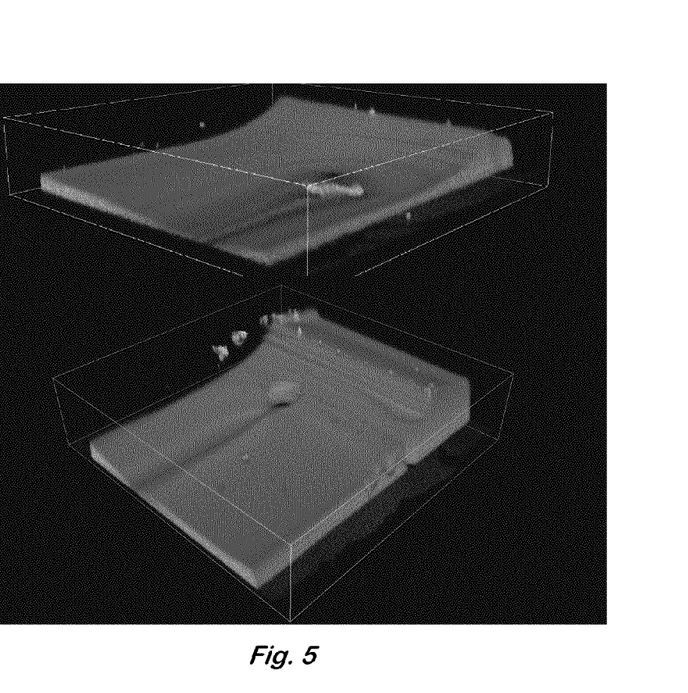
FIG. 5 shows confocal microscopy images of the conductive fluid layer, demonstrating effect of particles bound in the channel on the fluid flow profile. When the focused fluid layer is comparable in height to the bound particle, flow of the non-conductive focusing fluid is directed over the particle to create a non-conductive "shadow" downstream of the particle. This flow phenomenon represents an embodiment of the patent that may be promoted to amplify the signal measured due to presence of a particle.

In another embodiment, the target cell or particle binding sites can be oriented within the flow so that bound particles perturb the flow of liquids in a manner that amplifies the detected signal in a sensor. FIG. 5 shows confocal microscopy images demonstrating the shadowing effect that a particle imparts on the conductive path downstream from the particle. A particle of sufficient size relative to the conductive liquid layer in a flow focusing configuration enables flow of the conductive liquid around the sides of the particle while non-conductive liquid above the particle is re-directed from the confinement flow, over the particle, to create a non-conductive path or "shadow" downstream from the particle. The effective size of the insulating particle and insulating liquid shadow downstream may be promoted by design to create an amplified signal compared to that generated by the particle itself in a larger conductive fluid layer.

The Coulter counter is a well established instrument for the determination of the size distribution of particles (Coulter, U.S. Pat. No. 2,656,508). Its original design involves passing a suspension of particles through a small pore while the electrical conductivity through the pore is monitored. As a particle passes through the pore, it displaces some of the conductive solution, and causes a momentary increase in the impedance of the aperture. The magnitude of the impedance change is proportional to the size of the particle relative to the aperture size.

The dynamic range of the traditional design is set by the size of the aperture. In general, particles in the range of 2% to 60% of the diameter of the aperture can be counted. Samples containing a broad distribution in particle sizes present a problem, because a single large particle will clog the aperture.

Figure 6:
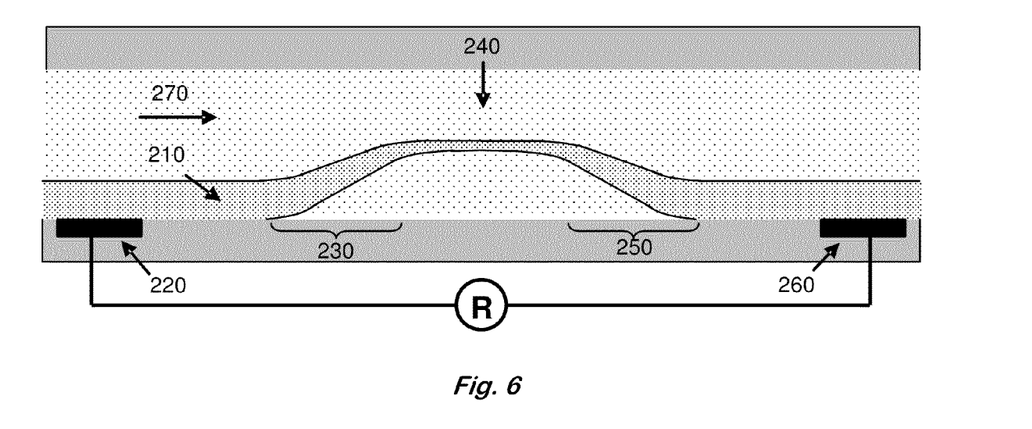
FIG. 6 shows a schematic of an embodiment that enables improvements to the standard Coulter counter. The conductive path is tailored by a sheath flow configuration.

In another embodiment, the solid aperture is replaced by a sheath of low conductivity fluid. As shown in FIG. 6, the conductive sample stream 210 is initially flowing down one side of the channel in contact with the wall, where the first electrode 220 will be placed. The sheathing is performed with a device configuration taught by U.S. patent application Ser. No. 11/423,225 (incorporated herein by reference) and does not require that the sample fluid pass through a channel constriction; thus eliminating the danger of clogging found in other designs. Instead a set of grooves in a sheathing region 230, placed in the top and bottom of the channel, wraps the sheath fluid 270 around the sample. The sheathing process also moves the sample stream from the low velocity region in contact with one wall, to a higher velocity region liquid-sheathed portion 240 in the center of the channel. As the sample stream accelerates, it is constricted. The configuration, allows electrical contact between the sensing electrodes and the conductive path. When particles are introduced into the conducting liquid, a spike in the impedance can be monitored as individual particles pass through the narrow portion of the sheathed region, indicating the presence and size of the particle. Adjustment of the relative flow rates of the conducting and non-conducting fluids may be used to selectively tune the sensitivity of the measurement for a given particle size, while avoiding issues of clogging that arise when relying on very small channel apertures. In an un-sheathing region 250, similar grooves are used to reverse the sheathing so that the conducting liquid can contact a second electrode 260.

Because operation is in the laminar flow regime, the sheathing process is reversible. A second set of grooves may un-sheath the sample, bringing it back into contact with the channel wall, where the second electrode will be placed. Since operation is in the Stokes flow regime, the dimensions of the channel are not critical; however, the channel may have widths below 1 mm. Sheath flow can be performed with core to sheath flow rate ratios in excess of 40,000. Cores as small as 16 microns have been produced in a 3 mm×1 mm channel. Smaller cores may be possible when smaller channels are used. The sensitivity will be a function of the degree to which the core stream is constricted as it passes through the interrogation region. The degree to which the core is constricted is strongly related to the flow rate ratio. Modeling of the flow behavior indicates a relationship of $C=1.21*R^{0.4766}$, where C is the degree of constriction and R is the flow rate ratio. When the flow rate of the conductive sample stream is $1/2000$ that of the nonconductive sheath, it will be constricted 30-fold in cross-section, as it passes through the interrogation region.

Disclosed herein are two designs that can produce fully sheathed flow in easily manufactured devices. The sheath and sample fluids are first introduced into the channel using conventional and easily manufactured geometries. Then a set of grooves wraps the sheath solution around the sample. The two designs require only one or two sheath inlets. They were designed and modeled using the in-house software, Tiny-Toolbox (TT). The diameter of the sheathed sample stream is governed by the relative flow rates of the sample and sheath streams, while the position and shape of the sample stream are controlled by the selection of the grooves.

Figure 7:
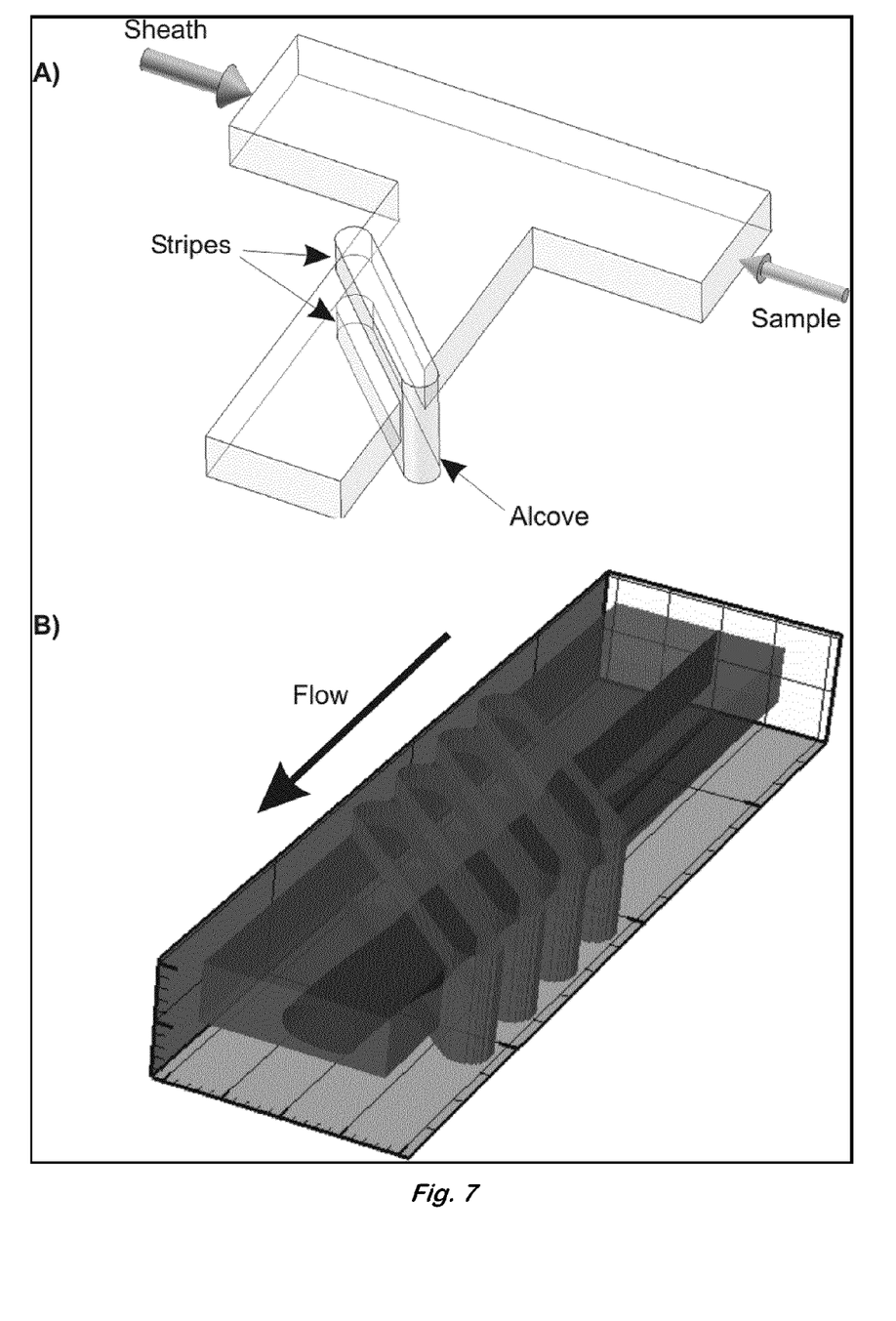

The stripe-based sheath flow design requires only a simple T-junction to establish the inflow condition (FIG. 7A), which places the sample and sheath streams side-by-side within the channel. A set of one or more grooves cut into the top and bottom of the channel then transfers a portion of the sheath solution over and under the sample stream and into a common alcove cut into the wall at the downstream end of the grooves. In transit, some fluid leaks out of the groove, isolating the sample stream from the top and bottom of the channel. The alcove becomes filled with the sheath fluid, which then exits along the wall of the main channel. Subsequent pairs of stripes move more sheath fluid to the far side of the sample stream and displace the sample stream further away from the wall. FIG. 7B shows the T3D simulation of a sheath and sample fluid traveling through a sheath device containing four pairs of grooves.

Figure 8:
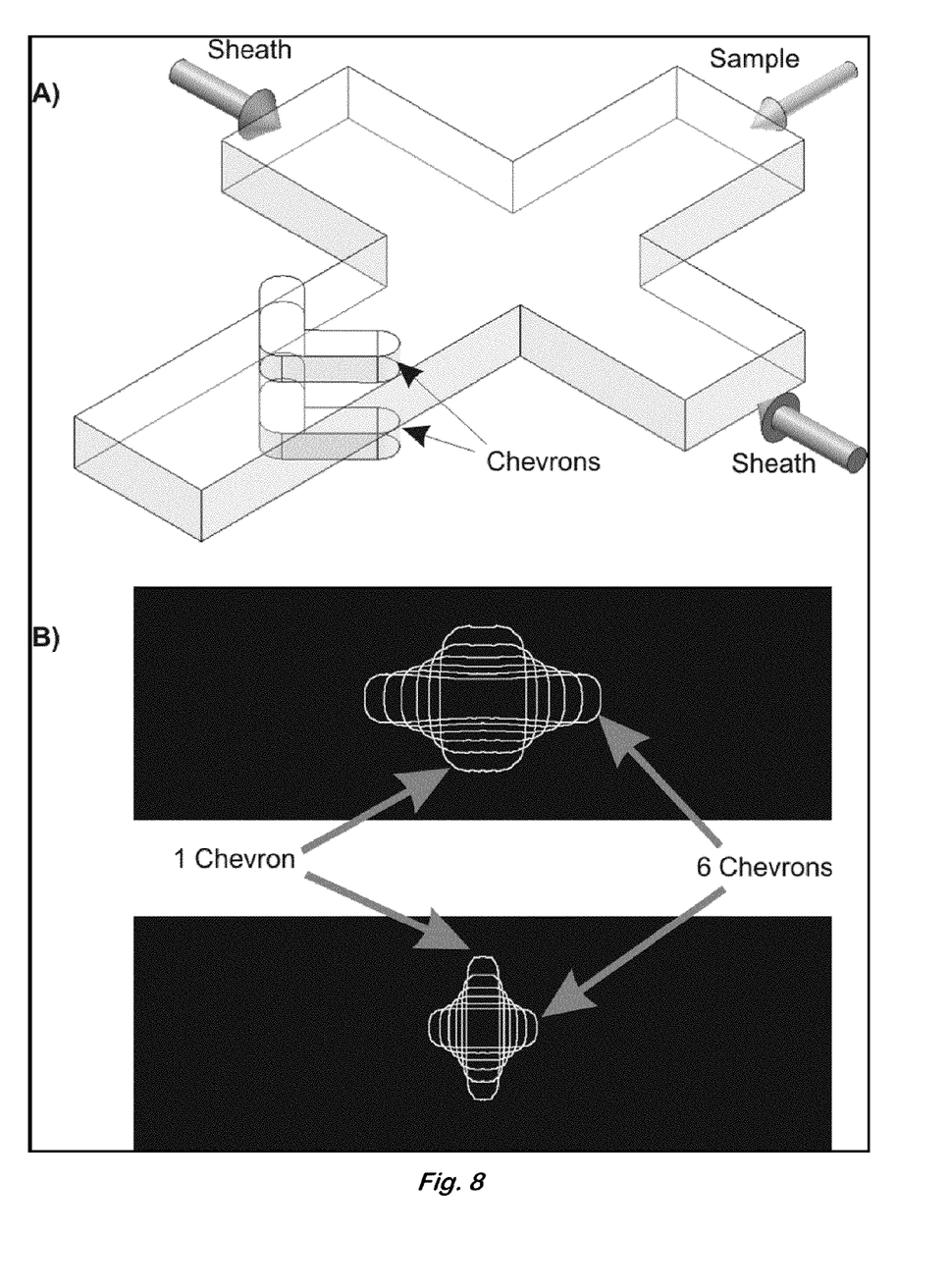

Another design can be seen in FIG. 8. In this design, the sheath solution is split equally between the two side inlets of a cross-intersection to place the sample stream in the center of the channel. A pair of chevrons cut into the top and bottom of the channel then transports sheath fluid from the sides to the middle along the top and bottom, isolating the sample stream from the top and bottom of the channel and compressing it vertically. As more chevron pairs are added, the sample is further compressed. FIG. 8B shows the outline of the sample stream for flow ratios of 4.5:1:4.5 and 9.5:1:9.5 as more chevron pairs are added to the channel.

Figure 16:
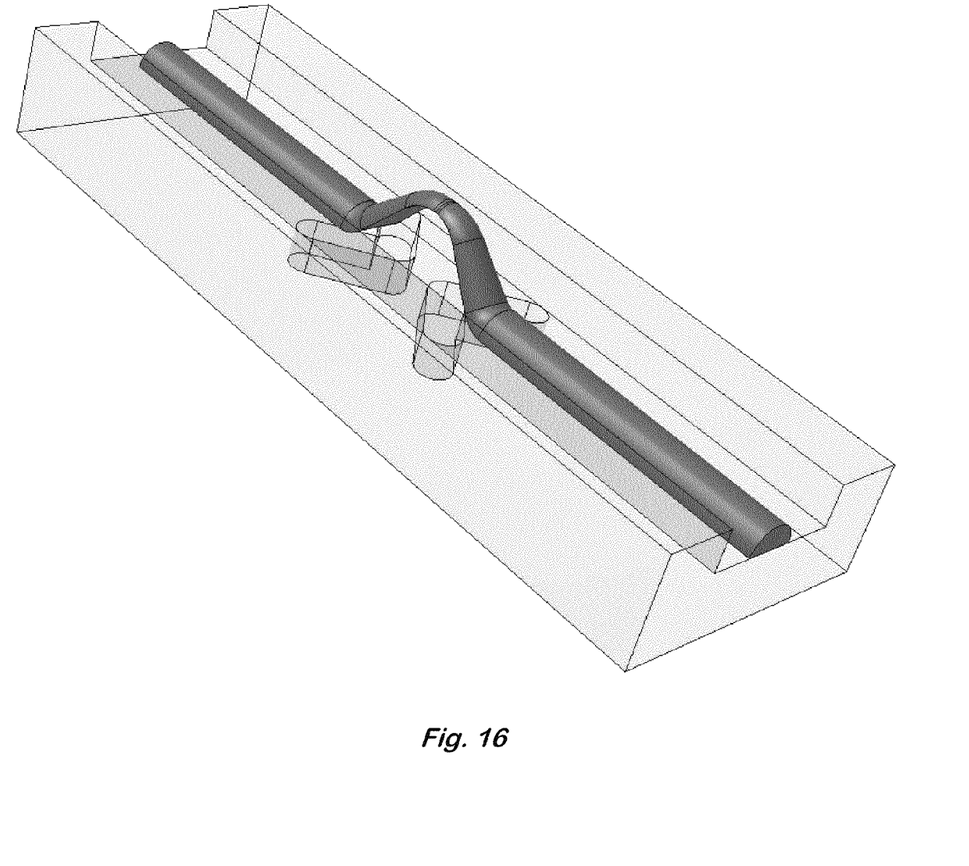
FIG. 16 shows a schematic diagram of a flow channel having both a sheathing fluid transporting structure and an unsheathing fluid transporting structure.

Unlike the groove-based design, the chevrons place the sample stream in the center of the channel, regardless of the flow ratios. Instead of moving to the side, the sample stream expands or contracts horizontally and symmetrically. Within limits, the height and width of the sample stream can be controlled independently. The number of chevron pairs controls the height of the sample stream while the flow ratio controls the width. FIG. 16 shows a channel having a sheathing chevron and an unsheathing chevron. The FIG. shows the flow of the liquid sample through the channel. The top surface of the channel, which may or may not also contain chevrons, is not shown.

Tailoring the conductive path for electrical detection measurements allows tunable detection sensitivity for different types/sizes of cells and particles in various configurations, while minimizing the detrimental effects of clogging when manipulating raw biological samples. The enhanced and adjustable sensitivity in a large channel that is amenable to flow of real samples is not possible with existing methods.

Having described the invention, the following examples are given to illustrate specific applications of the invention. The specific examples are not intended to limit the scope of the invention described in this application.

EXAMPLE 1

Figure 9:
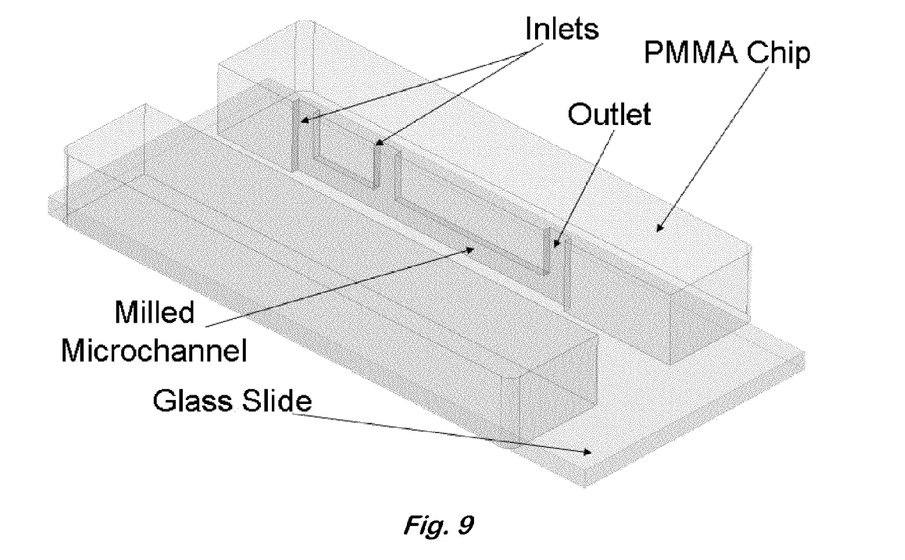
FIG. 9 shows a schematic of prototype device fabricated in PMMA by standard milling, then mounted with epoxy on a glass substrate containing thin film metal electrodes for sensing.
Figure 10:
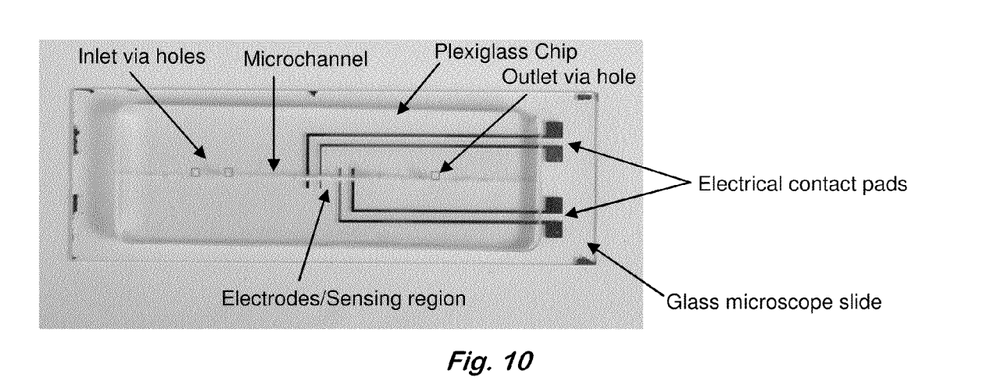
FIG. 10 shows a digital image (top view) of prototype device depicted in FIG. 9.
Figure 11:
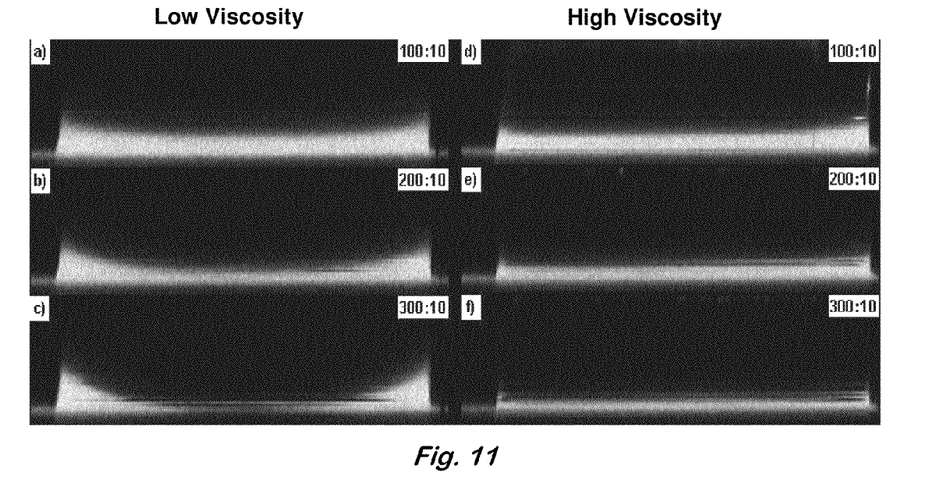
FIG. 11 shows cross-sectional images of the flow profile taken in the sensing region of the channel. Shape of the focused conducting fluid layer is imaged by confocal microscopy by obtaining the fluorescent signal from Rhodamine dye present in the fluid layer. Flow rate ratios of inlet 2:inlet1 were adjusted between 10:1, 20:1, and 30:1 to focus the fluid on the bottom surface of the channel. The viscosity of the liquids was adjusted using fructose. Images (a-c) correspond to fluids with no fructose while images (d-f) correspond to fluids with 40% fructose added to the aqueous based liquids.

Flow channel —FIGS. 9 and 10 are a schematic (top) and digital image (bottom) of a prototype channel fabricated in plexiglass and mounted with epoxy on a glass substrate containing thin-film metal electrodes. The channel was fabricated with a height of 250 microns. By the use of two plexiglass blocks, there was more precise control of the milling. It contained two inlets that were connected to standard syringe pumps and one outlet that led to a waste reservoir. The syringe pumps were used to implement pressure-driven flow inside the channel. The flow rate of fluid introduced into each inlet was controlled individually, and the flow rate ratio of one inlet relative to the other was used to focus fluid flow on the bottom surface of the channel as depicted in FIG. 1. The device was mounted on a confocal microscope to characterize the fluid flow profile in the channel to ensure proper flow focusing in the configuration depicted in FIG. 1. A rhodamine-based fluorescent dye was added to the confined fluid layer to visualize the flow profile during flow focusing experiments with the confocal microscope. FIG. 11 shows cross-sectional images of the channel fluid flow obtained from confocal fluorescence experiments where the flow rate ratio of inlet 2 to inlet 1 was adjusted between 10:1, 20:1, and 30:1 to focus the conductive liquid down to different sheet heights in the prototype channel. Fluid flows can be tailored by adjusting a variety of parameters such as flow rates, flow rate ratios, viscosity, channel geometry, channel size, etc. In this experiment, viscosity was adjusted with the addition of fructose to demonstrate the effect of such parameters on tailoring the shape of the flow profile. The low viscosity case in FIG. 11 corresponds to zero fructose, while the high viscosity case corresponds to 40% fructose in the conductive saline. The sheet height was monitored using a fluorescent dye and at the 30:1 flow rate ratio, high viscosity case shown in FIG. 11, the layer was measured to be 15 microns in height.

Figure 12:
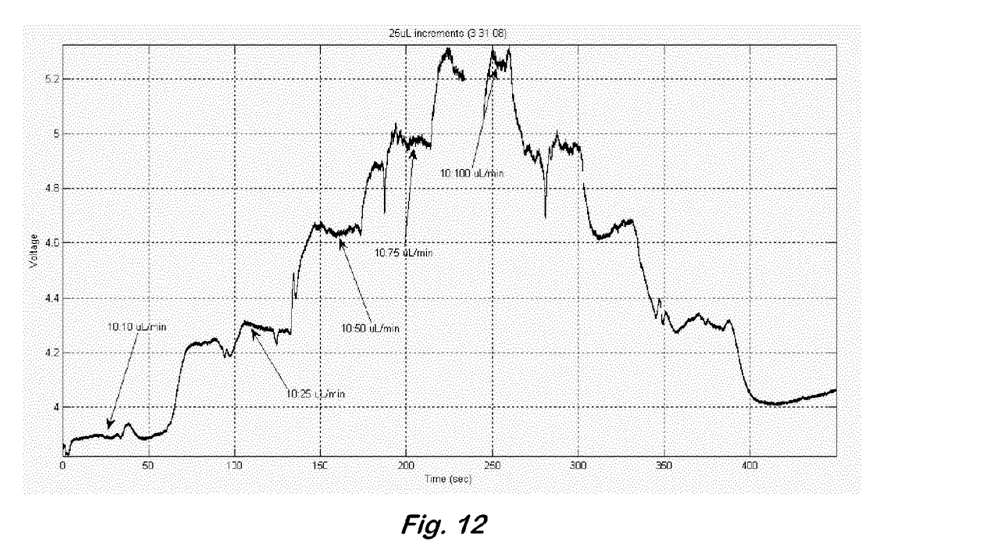
FIG. 12 shows raw data plotting the voltage difference measured in the device vs. time, for five flow rate ratios introduced at the inlets ranging between 1:1 and 10:1.
Figure 13:
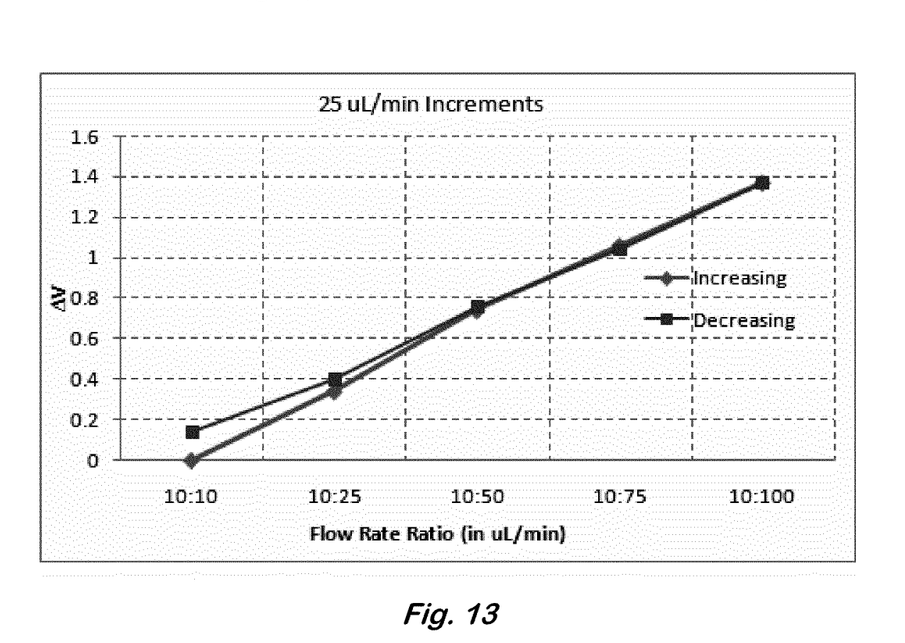
FIG. 13 shows a plot of voltage difference measured in the prototype device vs. flow rate ratio demonstrating linear change in sensor signal with decreasing conductive layer height. Data taken from average voltage measured at each plateau in FIG. 12 during the experiment.

Following confocal characterization of flow focusing studies in the prototype, electrical experiments were conducted by applying a 100 Hz, 250 nA alternating current to the outer electrodes (shown in FIGS. 2A and 10) while monitoring the corresponding potential difference between the inner sensing electrodes using a high-input impedance preamplifier connected to a lock-in amplifier referencing the driving frequency. FIG. 12 shows the raw data of the electrical response vs. time for the sensor prototype with variations in the flow rate ratio between inlet 2 (saline) and inlet 1 (DI water) varied between 1:1, and 10:1 as marked on each signal plateau in the figure. FIG. 13 shows the linear response of the sensor output vs. flow rate ratio; taking the average signal level from the raw data in FIG. 6 at each flow rate ratios. This data demonstrates that the signal is proportional to the height of the conducting layer. Reducing the thickness of the conducting layer, as would occur in the presence of insulating particles would thus change the voltage.

Figure 14:
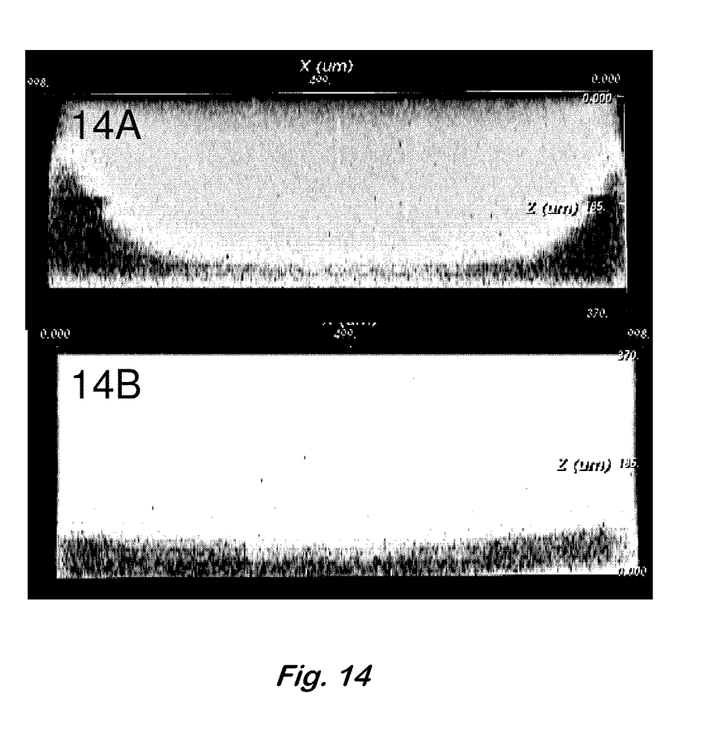
FIG. 14 shows confocal microscopy images of the concentration profile taken in two different flow focusing experiments.

FIGS. 14A and 14B show confocal microscopy images of the concentration profile taken in two different flow focusing experiments at a cross-section of the channel. In FIG. 14A the fluids were introduced as shown in FIG. 1, with the ionic fluid introduced through inlet 1, filling the channel prior to the introduction of the confining fluid. In this case, the thin layer of focused ionic fluid is on the side of the channel opposite the fluid inlets. In FIG. 14B, the inlets used by the two fluids are reversed with the confining fluid introduced through inlet 1 and filling the channel prior to the introduction of the ionic fluid. In this case the ionic fluid, introduced though inlet 2, is focused on the same side of the channel as the inlets.

Both experiments (14A-B) demonstrate an important characteristic of the flow profile at the edges of the channel; a curved profile that is most evident in FIG. 14A and present, yet more subtly so, in FIG. 14B. The curved effect is especially evident when increasing the flow ratio to push the limits of flow focusing, and it is also strongly dependent on the order with which the liquids are introduced and the surface on which focus the flow is focused. As electrical impedance measurements are combined with flow focusing, precise control of this flow profile may be maintained as it may define the conductive path and sensitivity of the electrical measurements. This curve in the profile in the channel corners may create the equivalent of an electrical short in the system and prevent high sensitivity measurements. Experimentally, it is seen that when focusing the first inlet fluid onto the bottom of the channel with the second fluid, the effect is more prevalent than when focusing the second inlet fluid on the top surface with the first fluid.

Figure 15:
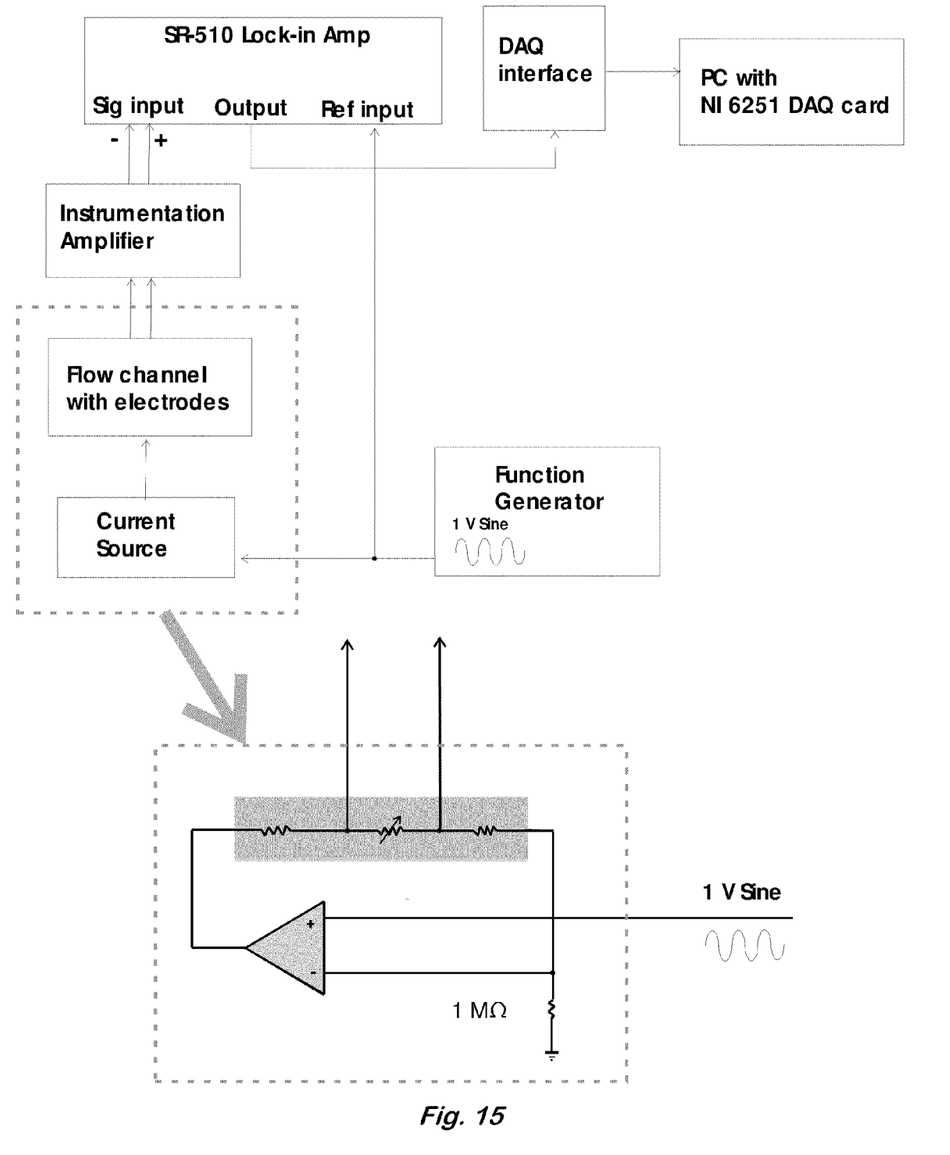
FIG. 15 is a schematic diagram of an example electrical detection setup.

FIG. 15 is a schematic diagram of the electrical detection setup used in this example. A function generator connected to a current source is used to produce the AC current that flows between the outer (current source) electrodes. The function generator also provides the reference signal for the lock-in amplifier. The inner (impedance detection) electrodes are connected to the lock-in amplifier through a low-noise instrumentation amplifier. To test the detection system, an op-amp circuit was designed and constructed to simulate the signals that would be generated between the impedance detection electrodes (circuit inside dotted box). The system was tested using the simulation circuit shown and was demonstrated to be appropriate for running coupled flow focusing-electrical impedance experiments.

EXAMPLE 2

Prophetic

Bead Binding—The procedure is the same as that in Example 1 which produced the data in FIG. 12 with a few additions. Neutravidin is immobilized on the surface of the channel between the sensing electrodes during fabrication of the testing device. The first step in the experiment is to vary the flow rate of DI water and saline as in FIG. 12. This produces a baseline which may be compared with the rest of the experiment. A suspension of borosilicate microbeads whose surface is functionalized with biotin is flowed in. The flow is stopped and ~10 minutes are allowed for the beads to settle and bind to the surface due to the standard biotin-neutravidin binding. The experiment as in FIG. 12 is repeated by flowing the DI water and saline in the channel simultaneously at different flow rate ratios. Differences in the signal as compared to the baseline curve would signify the presence of beads in the sensing region of the channel. In one trial, binding was not effective, but improved binding methods may be possible.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A device comprising:
   a laminar flow channel for liquids having an interior surface;
   one or more specific binding sites on the interior surface that can bind to a cell or particle of interest;
   two or more electrodes on the interior surface;
   wherein the binding sites are not on any of the electrodes;
   a confining fluid inlet positioned to flow a confining fluid through the channel;
   a sample inlet positioned to flow a conductive liquid between the confining fluid and the interior surface; and
   a meter for measuring the impedance of any fluid between the electrodes.

2. The device of claim 1, wherein the binding sites are between the two electrodes.

3. The device of claim 1, wherein the binding sites are between the electrodes and the sample inlet.

4. The device of claim 1, wherein the two or more electrodes and the meter comprise four electrodes configured as a four-electrode impedance meter.

5. The device of claim 1;
   wherein the specific binding sites are arranged in regions of the interior surface containing different types of specific binding sites; and
   wherein the device further comprises:
   two lateral confining fluid inlets positioned to flow the confining fluid in contact with the interior surface and the conductive liquid such that the conductive liquid contacts only one region at a time.

6. The device of claim 1, wherein the specific binding sites comprise an antibody, a DNA molecule, a sugar, an antimicrobial peptide, an aptamer, a cell receptor, a molecularly imprinted polymer, an antigen, a ligand, avidin, or lectin.

7. A device comprising:
   a laminar flow channel for liquids having an interior surface;
   one or more specific binding sites on the interior surface that can bind to a cell or particle of interest;
   wherein the specific binding sites are arranged in regions of the interior surface containing different types of specific binding sites;
   two or more electrodes on the interior surface;
   wherein the binding sites are not on any of the electrodes;
   a sample inlet positioned to flow a conductive liquid in contact with the interior surface;
   two lateral confining fluid inlets positioned to flow a confining fluid in contact with the interior surface and the conductive liquid such that the conductive liquid contacts only one region at a time; and
   a meter for measuring the impedance of any fluid between the electrodes.

8. A device comprising:
   a laminar flow channel for liquids;
   a confining fluid inlet positioned to flow a confining fluid through the channel;
   a sample inlet positioned to flow a liquid sample through the channel;
   two or more electrodes in the channel;
   at least one sheathing fluid transporting structure positioned so that the confining fluid forms a sheath around the liquid sample within a liquid-sheathed portion of the channel between the electrodes in which the liquid sample does not contact the channel;
   at least one unsheathing fluid transporting structure positioned so that the sheath is removed from around the liquid sample; and
   a meter for measuring the impedance of any fluid between the electrodes;
   wherein the electrodes are positioned to be in contact with the liquid sample in non-liquid-sheathed portions of the channel.

9. A method comprising:
   providing the device of claim 1;
   flowing the conductive liquid through the sample inlet and the channel and in contact with the electrodes and the binding sites;
   flowing the confining fluid, wherein confining fluid has a lower conductivity than the conductive liquid, through the confining fluid inlet and the channel at a rate that confines the conductive liquid to a confined portion of the channel that is adjacent to the electrodes and the binding sites; and
   measuring the impedance between the electrodes.

10. The method of claim 9, wherein the specific binding sites comprise an antibody, a DNA molecule, a sugar, an antimicrobial peptide, an aptamer, a cell receptor, a molecularly imprinted polymer, an antigen, a ligand, avidin, or lectin.

11. The method of claim 9, wherein the conductive liquid does not cause denaturation of the specific binding sites.

12. The method of claim 9, wherein the conductive liquid is a liquid sample suspected of containing a cell or particle that specifically binds to the binding sites.

13. The method of claim 12, wherein the liquid sample comprises a culture medium, a clinical sample, a food extract, a beverage, an environmental sample, diesel fuel, an industrial process stream, or seawater.

14. The method of claim 9, wherein the conductive liquid is an aqueous salt solution, an ionic buffer, physiological saline, or an ionic liquid.

15. The method of claim 9, wherein the confining fluid has a viscosity that does not create turbulence when flowing adjacent to the liquid sample.

16. The method of claim 9, wherein the confining fluid is deionized water, glycerol, an aqueous sugar solution, an alcohol, or an aqueous poly(vinyl alcohol) solution.

17. The method of claim 9, further comprising:
flowing a liquid sample through the sample inlet and the channel and in contact with the binding sites before flowing the conductive liquid.

18. The method of claim 17, wherein the confining fluid has a viscosity that does not create turbulence when flowing adjacent to the liquid sample.

19. The method of claim 17, wherein flowing the liquid sample occurs without flowing the confining fluid.

20. A method comprising:
providing the device of claim 5;
flowing the conductive liquid through the sample inlet and the channel and in contact with the electrodes and the binding sites;
flowing the confining fluid, wherein confining fluid has a lower conductivity than the conductive liquid, through the confining fluid inlet and the channel at a rate that confines the conductive liquid to a confined portion of the channel that is adjacent to the electrodes and the binding sites;
flowing the confining fluid into the two lateral confining fluid inlets such that the conductive liquid contacts only a first region of the regions;
performing a first measurement of the impedance between the electrodes;
adjusting the flow rate through the lateral confining fluid inlets so that the conductive liquid contacts only a second region of the regions; and
performing a second measurement of the impedance between the electrodes.

21. The method of claim 20, wherein the conductive liquid is a liquid sample suspected of containing a cell or particle that specifically binds to the binding sites.

22. The method of claim 20, further comprising:
flowing a liquid sample through the channel and in contact with the binding sites before flowing the conductive liquid.

23. The method of claim 22, wherein flowing the liquid sample occurs without flowing the confining fluid.

24. The method of claim 22, further comprising:
flowing the confining fluid into the two lateral confining fluid inlets such that the liquid sample contacts only the first region; and
adjusting the flow rate through the lateral confining fluid inlets so that the liquid sample contacts only the second region.

25. A method comprising:
providing the device of claim 7
flowing the conductive liquid through the sample inlet and the channel and in contact with the electrodes and the binding sites;
flowing the confining fluid, wherein confining fluid has a lower conductivity than the conductive liquid, into the two lateral confining fluid inlets such that the conductive liquid contacts only a first region of the regions;
performing a first measurement of the impedance between the electrodes;
adjusting the flow rate through the lateral confining fluid inlets so that the conductive liquid contacts only a second region of the regions; and
performing a second measurement of the impedance between the electrodes.

26. A method comprising:
providing the device of claim 8;
flowing the liquid sample through the sample inlet and the channel and in contact with the electrodes;
flowing the confining fluid, wherein confining fluid has a lower conductivity than the liquid sample, through the confining fluid inlet and the channel at a rate that confines the liquid sample to a confined portion of the channel that is adjacent to the electrodes; and
measuring the impedance between the electrodes.

27. The method of claim 26, wherein the liquid sample comprises a culture medium, a clinical sample, a food extract, a beverage, an environmental sample, diesel fuel, an industrial process stream, or seawater.

28. The method of claim 26, wherein the confining fluid has a viscosity that does not create turbulence when flowing adjacent to the liquid sample.

29. The method of claim 26, wherein the confining fluid is deionized water, glycerol, an aqueous sugar solution, an alcohol, or an aqueous poly(vinyl alcohol) solution.

* * * * *